United States Patent [19]

Meyers et al.

[11] Patent Number: 5,797,908
[45] Date of Patent: Aug. 25, 1998

[54] EXTERNAL FIXATOR ASSEMBLY AND CLAMP THEREFOR

[75] Inventors: John E. Meyers, Columbia City; Gregory G. Price, Warsaw; Randall N. Allard, Plymouth, all of Ind.

[73] Assignee: Bristol-Myers Squibb Company, New York, N.Y.

[21] Appl. No.: 794,074

[22] Filed: Feb. 4, 1997

[51] Int. Cl.⁶ .................................. A61B 17/62
[52] U.S. Cl. .................. 606/54; 606/56; 606/59
[58] Field of Search ..................... 606/54, 55, 56, 606/57, 58, 59, 60, 61, 72, 73

[56] References Cited

U.S. PATENT DOCUMENTS

| | | | |
|---|---|---|---|
| D. 367,531 | 2/1996 | Price et al. | D24/143 |
| D. 373,635 | 9/1996 | Price et al. | D24/140 |
| 4,308,863 | 1/1982 | Fischer | 128/92 A |
| 4,356,571 | 11/1982 | Esper et al. | 3/1 |
| 4,365,624 | 12/1982 | Jaquet | 128/92 A |
| 4,502,473 | 3/1985 | Harris et al. | 128/92 A |
| 4,535,763 | 8/1985 | Jaquet | 18/92 A |
| 4,620,533 | 11/1986 | Mears | 128/92 Z |
| 4,624,249 | 11/1986 | Alavarez | 128/92 ZK |
| 4,768,524 | 9/1988 | Hardy | 128/92 Z |
| 4,784,125 | 11/1988 | Monticelli et al. | 128/92 Z |
| 4,848,368 | 7/1989 | Kronner | 128/92 Z |
| 4,889,111 | 12/1989 | Ben-Dov | 128/419 F |
| 4,893,618 | 1/1990 | Herzberg | 606/54 |
| 4,902,297 | 2/1990 | Devanathan | 623/16 |
| 4,923,458 | 5/1990 | Fischer | 606/59 |
| 4,936,843 | 6/1990 | Sohngen | 606/54 |
| 4,941,481 | 7/1990 | Wagenknecht | 606/59 |
| 4,978,348 | 12/1990 | Llizarov | 606/57 |
| 4,978,350 | 12/1990 | Wagenknecht | 606/72 |
| 5,019,077 | 5/1991 | Bastiani et al. | 606/527 |
| 5,021,054 | 6/1991 | Monfardini et al. | 606/54 |
| 5,064,439 | 11/1991 | Chang et al. | 623/66 |
| 5,067,954 | 11/1991 | Llizarov | 606/58 |
| 5,087,258 | 2/1992 | Schewior | 606/56 |
| 5,095,919 | 3/1992 | Monticelli et al. | 606/56 |
| 5,098,432 | 3/1992 | Wagenknecht | 606/54 |
| 5,112,331 | 5/1992 | Miletich | 606/53 |
| 5,152,687 | 10/1992 | Amino | 433/173 |
| 5,163,962 | 11/1992 | Salzstein et al. | 623/23 |
| 5,167,661 | 12/1992 | Wagenknecht | 606/54 |
| 5,181,930 | 1/1993 | Dumbleton et al. | 623/23 |
| 5,192,330 | 3/1993 | Chang et al. | 606/22 |
| 5,207,676 | 5/1993 | Canadell et al. | 606/54 |
| 5,275,598 | 1/1994 | Cook | 606/54 |
| 5,275,599 | 1/1994 | Abikowski et al. | 523/54 |
| 5,314,426 | 5/1994 | Pohl et al. | 606/58 |
| 5,397,358 | 3/1995 | Wenner et al. | 623/16 |
| 5,397,365 | 3/1995 | Trentacosta | 623/18 |
| 5,439,465 | 8/1995 | Tumibay | 606/105 |
| 5,443,464 | 8/1995 | Russell et al. | 606/54 |
| 5,443,513 | 8/1995 | Moumene et al. | 623/16 |
| 5,458,599 | 10/1995 | Adobbati | 606/56 |

FOREIGN PATENT DOCUMENTS

| | | |
|---|---|---|
| 0 159 007 A2 | 10/1985 | European Pat. Off. . |
| 0 517 939 A1 | 12/1992 | European Pat. Off. . |
| 2 499 400 | 8/1982 | France . |
| 2 101 488 | 1/1983 | United Kingdom . |

OTHER PUBLICATIONS

Zimmer, Inc.–Brochure–Torus External Fixation System–Lt. No. 97–2613–01 Rev. 1–1993.

*Primary Examiner*—Michael Buiz
*Assistant Examiner*—David O. Reip
*Attorney, Agent, or Firm*—Todd A. Dawson

[57] ABSTRACT

The invention is directed to an external fixator assembly for externally fixating and stabilizing a bone. The external fixator assembly includes a frame member; a bone piercing member insertable into the bone; and a clamp. The clamp includes a body with a slot, a hole, and a threaded opening therein. The threaded opening is in communication with the slot. The bone piercing member is received within the hole. The frame member is disposed within the slot. The clamp further includes a set screw in the threaded opening. The set screw is engaged with the frame member and holds the frame member within the slot.

16 Claims, 3 Drawing Sheets

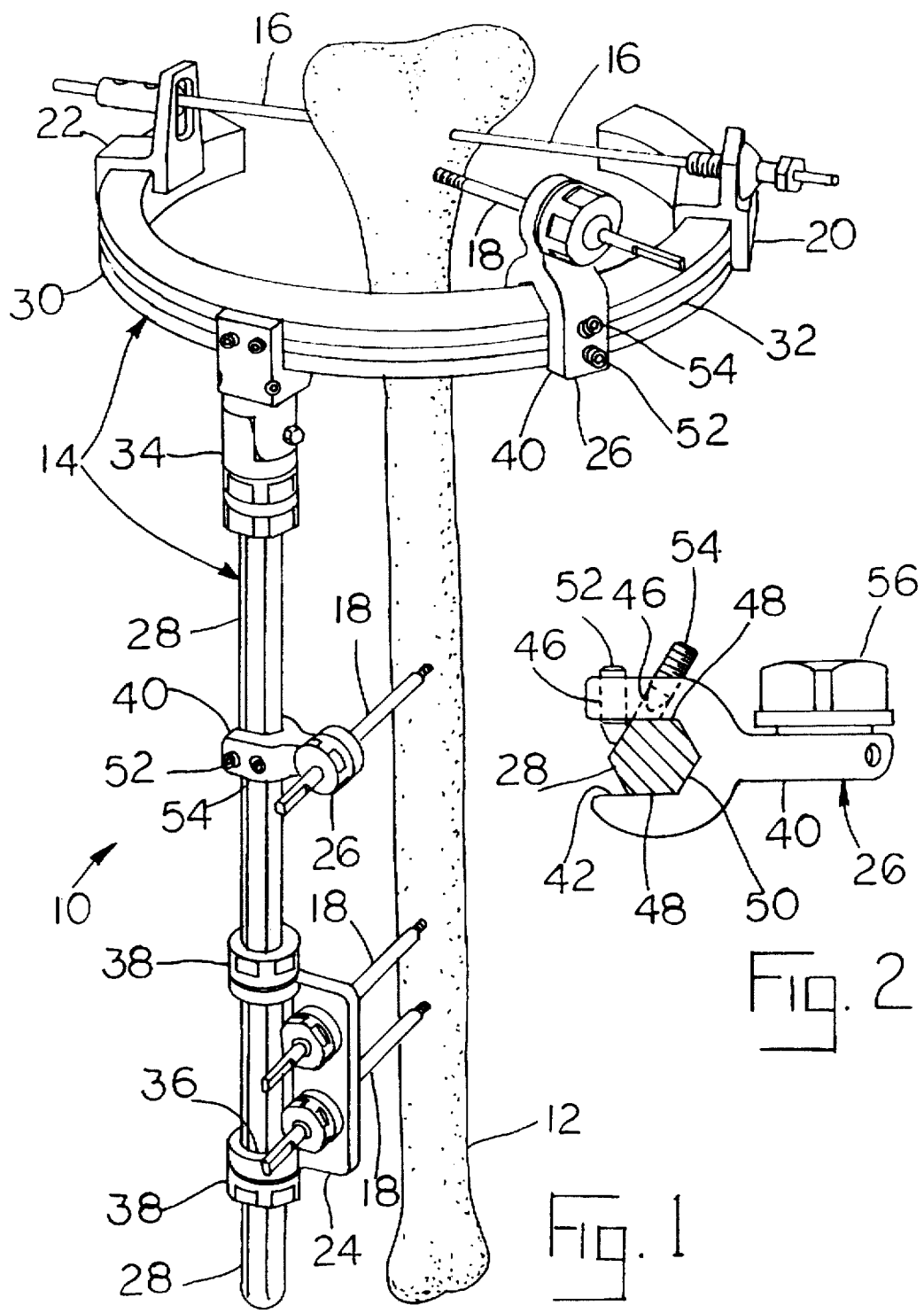

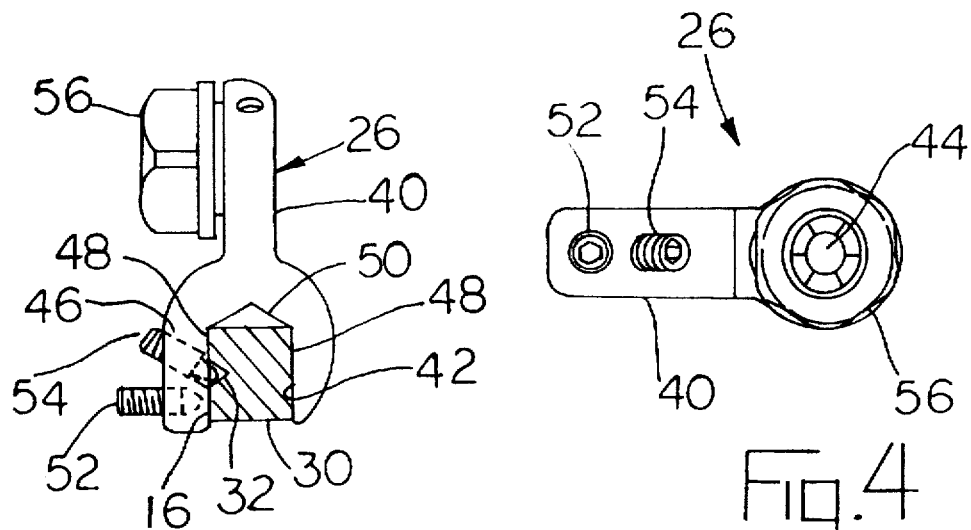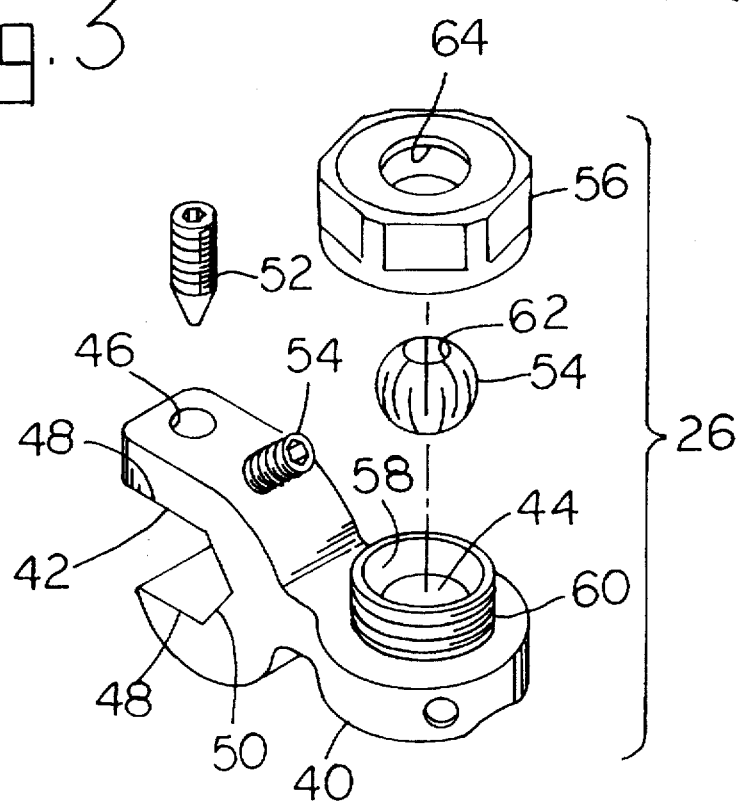

EXTERNAL FIXATOR ASSEMBLY AND CLAMP THEREFOR

BACKGROUND OF THE INVENTION

1. Field of the Invention.

The present invention relates to external fixator assemblies used for externally fixating and stabilizing a bone, and, more particularly, to a clamp attachable to a rod or ring in such an external fixator assembly.

2. Description of the Related Art.

An external fixator assembly is used to externally fixate and stabilize a bone, such as a femur or tibia. The external fixator assembly typically includes a frame which is disposed adjacent to the patient at the site where the fixator assembly is to be used. For example, if a tibia is to be externally fixated, the frame may include a fixation rod which extends substantially parallel to the axis of the tibia and a ring which is attached to one end of the fixation rod and at least partially encircles the leg of the patient. A plurality of clamps are typically attached to the fixation rod and ring at selected locations. The clamps are attached to bone piercing members which are inserted into the tibia. The bone piercing members may be in the form of a fixation pin, wire and/or buttress pin. An example of such an external fixator assembly is disclosed in U.S. Pat. No. 5,443,464 (Russell, et al.).

Conventional clamps for attachment with the fixation rod typically include a body with a centrally located opening therein. A retainer nut is threadingly attached to the body of the clamp and biases a collet against a seat formed around the opening. The fixation rod extends through the retaining nut, collet and opening in the body, and is locked into position relative to the body by tightening the retaining nut.

A problem with a clamp as described above is that the clamp must be slid over an end of the fixation rod and moved along the length of the rod to a desired longitudinal position. Accordingly, if it becomes necessary during a surgical procedure to add an additional clamp between two already existing clamps, at least one of the clamps may need to be removed from the fixation rod to allow the new clamp to be slid into place. Conventional clamps may therefore not allow an additional clamp to be easily attached to the fixation rod. Moreover, such a clamp is not attachable to the ring of the frame.

Clamps which are attachable to the ring of the frame typically include a body having a C-shaped opening. The ring is positioned within the C-shaped opening of the body. A set screw is disposed in a leg of the body defining the C-shaped opening and biases the ring toward the opposing leg of the body. Such a clamp may be attached to the ring as described, but is not attachable to the fixation rod of the frame.

It is also known to provide a clamp for a fixation rod having a clam-shell configuration with two generally semi-circular parts which clamp around the fixation rod. The two parts of the clam-shell shaped clamp may be attached to each other using screws at the mating ends. Alternatively, the two parts of the clam-shell shaped clamp may be hingedly connected together at one pair of adjacent ends and fastened via screws at the other pair of adjacent ends.

What is needed in the art is a clamp which may be attachable to either a fixation rod or a ring of a frame, and which allows additional clamps to be added at any desired location on the frame during surgery.

SUMMARY OF THE INVENTION

The present invention provides an external fixator assembly including a clamp which may be slid over and selectively engaged with either a fixation rod or a ring.

The invention comprises, in one form thereof, an external fixator assembly for externally fixating and stabilizing a bone. The external fixator assembly includes a frame member; a bone piercing member insertable into the bone; and a clamp. The clamp includes a body with a slot, a hole, and a threaded opening therein. The threaded opening is in communication with the slot. The bone piercing member is received within the hole. The frame member is disposed within the slot. The clamp further includes a set screw in the threaded opening. The set screw is engaged with the frame member and holds the frame member within the slot.

An advantage of the present invention is that the clamp may be selectively engaged with either a fixation rod or a ring.

Another advantage is that the clamp may be slid over a frame member, such as a fixation rod or ring, from the side rather than the end of the frame member.

Yet another advantage is that the frame member is biased into the slot in the clamp using a set screw.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a perspective view of an external fixator assembly including an illustration of one embodiment of a clamp of the present invention;

FIG. 2 is an end view of the clamp shown in FIG. 1 when attached to the hexagonal rod;

FIG. 3 is an end view of the clamp shown in FIG. 1 when attached to the partial ring;

FIG. 4 is a plan view of the clamp of the present invention shown in FIGS. 1–3;

FIG. 5 is an exploded, perspective view of the clamp of the present invention shown in FIGS. 1–4; and FIG. 6 is a perspective view of another embodiment of a clamp of the present invention having two holes therein for receiving fixation pins or the like.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 6:
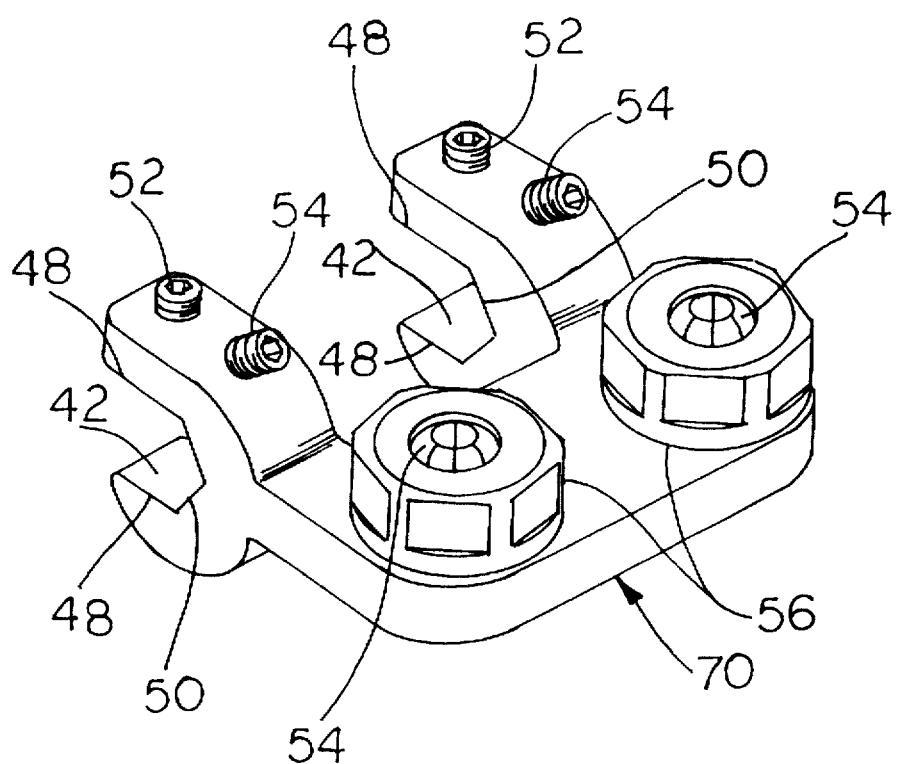

Referring now to the drawings and particularly to FIG. 1, there is shown an embodiment of an external fixator assembly 10 for externally fixating and stabilizing a bone, such as a tibia 12. External fixator assembly 10 generally includes a frame 14, bone piercing members 16, 18 and clamps 20, 22, 24 and 26.

Frame 14 includes one or more frame members, such as a hexagonal fixation rod 28 and/or ring 30. Ring 30 is a partial ring which is configured to extend partially around a limb of the patient. Ring 30 includes a groove 32 which may receive a set screw associated with a clamp, as will be described hereinafter. Rod 28 and ring 30 are connected together via a connector 34.

Bone piercing members 16, 18 are insertable into bone 12 and anchor bone 12 relative to frame 14. Bone piercing member 16 is in the form of a wire extending through bone 12 and between clamps 20 and 22. Bone piercing members 18 are in the form of fixation pins having a threaded end which is screwed into bone 12. Other types of bone piercing members such as a buttress pin (not shown) which abuts and may slightly penetrate bone 12 are also possible.

Clamps 20 and 22 are of conventional design and include a generally C-shaped opening (not numbered), in which ring 30 is disposed. Clamps 20 and 22 are not attachable with rod 28.

Clamp 24 is also of conventional design and is configured for carrying two fixation pins 18. Clamp 24 includes a body having a pair of openings (one of which is referenced 36 in FIG. 1), and a pair of retaining nuts 38 associated with each opening. Retaining nuts 38 lock the body of clamp 24 relative to rod 28 when tightened. Clamp 24 is not attachable to ring 30.

According to the present invention, and referring to FIGS. 1-5, conjunctively, clamp 26 is attachable to either of rod 28 or ring 30, and may be added during a surgical procedure without removal of any other adjacent clamps. Clamp 26 includes a body 40 with a slot 42, hole 44 and pair of threaded openings 46 therein. Hole 44 is sized and configured to receive a bone piercing member such as a wire 16 or fixation pin 18. Threaded openings 46 are formed in body 40 and are in communication with slot 42. Slot 42 is sized and configured to receive either of rod 28 or ring 30 therein. More particularly, slot 42 is a generally U-shaped slot having two substantially parallel walls 48 with an interconnecting wall 50 extending between parallel walls 48. Interconnecting wall 50 includes two adjacent wall segments which are disposed at an obtuse angle relative to each other which closely approximates the angle between adjacent wall segments of fixation rod 28. Accordingly, when engaged with rod 28, parallel walls 48 and the two adjacent wall segments of interconnecting wall 50 lie closely adjacent to four sides of rod 28, as shown in FIG. 2.

Clamp 26 also includes a pair of set screws 52, 54 received within a corresponding threaded opening 46. Set screw 52 and the corresponding threaded opening 46 are positioned within body 40 to engage fixation rod 28 (FIG. 2), and set screw 54 and the corresponding threaded opening 46 are positioned within body 40 to engage ring 30 (FIG. 3). When clamp 26 is engaged with rod 28, set screw 52 engages a wall of rod 28 and thereby biases rod 28 toward interconnecting wall 50. On the other hand, when clamp 26 is engaged with ring 30, set screw 54 is received within groove 32 of ring 30 and biases ring 30 against the opposing parallel wall 48.

In the embodiment shown, threaded openings 46 and set screws 52, 54 are each disposed in communication with the same parallel wall 48. However, it is to be understood that set screw 52 and threaded opening 46 may be disposed in association with one parallel wall 48 and the other set screw 54 and threaded opening 46 may be disposed in association with the other parallel wall 48.

In the particular embodiment shown in the drawings, clamp 26 also includes a collet 54 and retaining nut 56 which are engaged with body 40 (FIG. 5). More particularly, body 40 includes a seat 58 which surrounds hole 44, and an externally threaded portion 60 which surrounds seat 58. Collet 54 includes an aperture 62 therein, and retaining nut 56 includes a central opening 64 therein. A bone piercing member such as fixation pin 18 is received within each of hole 44, aperture 62 and central opening 64. Retaining nut 56 threadingly engages external threads 60 and biases collet 54 into seat 58. Seat 58, in known manner, in turn exerts a radially inward force on collet 54 which grasps fixation pin 18 and locks clamp 26 relative to fixation pin 18.

During use, clamp 26 may be selectively attached to either fixation rod 28 or ring 30 at any desired location. Clamp 26 may be slid onto rod 28 or ring 30 from the end or from the side to any desired attachment location. If clamp 26 is attached to rod 28, body 40 is slid over rod 28 such that rod 28 is disposed within slot 42. Set screw 52 is then tightened to lock body 40 relative to rod 28. On the other hand, if clamp 26 is attached to ring 30, body 40 is slid onto ring 30 such that ring 30 is disposed within slot 42. Set screw 54 is then tightened against ring 30 within groove 32 to lock clamp 26 in place relative to ring 30.

FIG. 6 illustrates another embodiment of a clamp 70 of the present invention. Clamp 70 is similar to clamp 26 shown in FIGS. 1-5. However, clamp 70 includes two generally U-shaped slots 42 which engage a frame member such as rod 28 or ring 30 at two different locations. Each slot 42 includes a pair of set screws 52, 54 for locking clamp 70 into place with rod 28 or ring 30, respectively, as described above. Clamp 70 also includes two holes (not shown) which are respectively associated with a collet 54 and retaining nut 56.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An external fixator assembly for externally fixating and stabilizing a bone, said external fixator assembly comprising:

a frame member;

a bone piercing member insertable into the bone; and a clamp including a body with a U-shaped slot, a hole, and a threaded opening therein, said threaded opening being in communication with said slot, said bone piercing member being received within said hole, said frame member being disposed within said slot, said clamp further including a set screw in said in said threaded opening, said set screw being engaged with said frame member and holding said frame member within said slot;

wherein said U-shaped slot has an interconnecting wall comprising two adjacent wall segments of substantially equal length which abut at a center point to form an obtuse angle.

2. The external fixator assembly of claim 1, wherein said U-shaped slot further comprises two substantially parallel walls with said interconnecting wall between said parallel walls, said threaded opening being disposed in one of the parallel walls.

3. The external fixator assembly of claim 2, wherein said set screw is positioned to bias said frame member toward said interconnecting wall.

4. The external fixator assembly of claim 1, wherein said clamp body further comprises a seat surrounding said hole and an externally threaded portion surrounding said seat, and wherein said clamp further comprises a collet with an aperture therein and a retaining nut with a central opening therein, said bone piercing member being received within each of said aperture and said central opening, said collet being disposed adjacent said seat and said retaining nut being threadingly engaged with said externally threaded portion and biasing said collet against said seat.

5. The external fixator assembly of claim 1, wherein said bone piercing member comprises one of a fixation pin, wire and buttress pin.

6. The external fixator assembly of claim 1, wherein said frame member comprises one of a fixation rod and a ring.

7. The external fixator assembly of claim 6, wherein said fixation rod comprises a hexagonal rod.

8. An external fixator assembly for externally fixating and stabilizing a bone, said external fixator assembly comprising:

a rod;

a ring connected to said rod;

a bone piercing member insertable into the bone; and a clamp including a body with a U-shaped slot, a hole, and at least one threaded opening therein, each said threaded opening being in communication with said slot, said bone piercing member being received within said hole, said slot being sized and configured to selectively receive either of said rod and said ring therein, said clamp further including at least one set screw received within a corresponding said threaded opening, at least one of the said set screws being engaged with said selected one of said rod and ring;

wherein said U-shaped slot has an interconnecting wall comprising two adjacent wall segments of substantially equal length which abut at a center point to form an obtuse angle.

9. The external fixator assembly of claim 8, wherein said at least one threaded opening comprises two threaded openings and wherein said at least one set screw comprises two set screws, each said set screw being received within a respective said threaded opening.

10. The external fixator assembly of claim 9, wherein one of said set screws is positioned to engage said rod and an other of said set screws in positioned to engage said ring.

11. The external fixator assembly of claim 10, wherein said U-shaped slot further comprises two substantially parallel walls with said interconnecting wall between said parallel walls, each said threaded opening being in communication with one of said parallel walls, each said set screw being positioned to bias said ring or said rod toward said interconnecting wall.

12. The external fixator assembly of claim 11, wherein each said threaded opening is disposed in a same said parallel wall.

13. The external fixator assembly of claim 8, wherein said clamp body further comprises a seat surrounding said hole and an externally threaded portion surrounding said seat, and wherein said clamp further comprises a collet with an aperture therein and a retaining nut with a central opening therein, said bone piercing member being received within each of said aperture and said central opening, said collet being disposed adjacent said seat and said retaining nut being threadingly engaged with said externally threaded portion and biasing said collet against said seat.

14. The external fixator assembly of claim 8, wherein said bone piercing member comprises one of a fixation pin, wire and buttress pin.

15. The external fixator assembly of claim 8, wherein said ring comprises a partial ring.

16. The external fixator assembly of claim 8, wherein said rod comprises a hexagonal rod.

* * * * *